(12) United States Patent
McMahon et al.

(10) Patent No.: US 9,408,818 B2
(45) Date of Patent: *Aug. 9, 2016

(54) METHOD FOR THE UTILIZATION OF AND PRODUCT CONTAINING INACTIVATED PROBIOTIC

(75) Inventors: Robert J. McMahon, Evansville, IN (US); William Michael Russell, Evansville, IN (US); Udo Herz, Evansville, IN (US); Josef Neu, Gainesville, FL (US)

(73) Assignee: Mead Johnson Nutrition Company, Glenview, IL (US)

( * ) Notice: Subject to any disclaimer, the term of this patent is extended or adjusted under 35 U.S.C. 154(b) by 1950 days.

This patent is subject to a terminal disclaimer.

(21) Appl. No.: 12/035,705

(22) Filed: Feb. 22, 2008

(65) Prior Publication Data

US 2008/0206212 A1 Aug. 28, 2008

Related U.S. Application Data

(60) Provisional application No. 60/904,122, filed on Feb. 28, 2007.

(51) Int. Cl.
*A61K 31/202* (2006.01)
*A61K 35/745* (2015.01)
*A61K 35/747* (2015.01)

(52) U.S. Cl.
CPC ............ *A61K 31/202* (2013.01); *A61K 35/745* (2013.01); *A61K 35/747* (2013.01)

(58) Field of Classification Search
CPC ............ A61K 2300/00; A61K 35/747; A61K 31/702; A61K 31/715; A61K 35/741; A61K 35/745; A61K 36/06; A61K 31/13; A61K 31/195; A61K 31/198; A61K 31/355; A61K 31/192; A61K 31/415; A61K 35/18; A61K 35/52; A61K 45/00; A61K 31/202; A61K 31/201; A61K 35/20; A61K 35/74; A61K 45/06; A61K 35/744; A61K 31/4164; A61K 31/454; A61K 31/496; A61K 31/519; A61K 31/52; A61K 31/5375; A61K 31/606; A61K 31/635; A61K 38/13; A23V 2002/00; A23V 2200/3204; A23V 2200/3202; A23V 2200/324; A23V 2200/32; A23V 2250/18
See application file for complete search history.

(56) References Cited

U.S. PATENT DOCUMENTS

2001/0036453 A1 11/2001 Reid et al.
2005/0180962 A1 8/2005 Raz et al.
2006/0233762 A1 10/2006 McMahon et al.

FOREIGN PATENT DOCUMENTS

| EP | 1364586 A1 | 5/2002 |
|---|---|---|
| WO | WO 2004/069156 A2 | 8/2004 |
| WO | WO 2004/112508 A1 | 12/2004 |
| WO | WO 2006/108824 A1 | 10/2006 |
| WO | WO 2006/113034 A1 | 10/2006 |
| WO | 2006/124630 | * 11/2006 |
| WO | WO 2006/124630 A2 | 11/2006 |

OTHER PUBLICATIONS

Jeschke, et al., *Insulin Attenuates the Systemic Inflammatory Response to Thermal Trauma*, Mol. Med. 8(8):443-450 (2002).
Van Woensel, J., et al., *Viral Lower Respiratory Tract Infection in Infants and Young Children*, BMJ 327:36-40 (2003).
Murch, S.H., *Toll of Allergy Reduced by Probiotics*, Lancet, 357:1057-1059 (2001).
Hooper, et al., *How Host-Microbial Interactions Shape the Nutrient Environment of the Mammalian Intestine*, Annu. Rev. Nutr. 22:283-307 (2002).
Bourlioux, et al., *The Intestine and its Microflora are Partners for the Protection of the host: Report on the Danone Symposium "The Intelligent Intestine,"* held in Paris, Jun. 14, 2002, Am. J. Clin. Nutr. 78:675 (2003).
Hooper, L.V., & Gordon, J.I., *Commensal Host-Bacterial Relationships in the Gut*, Sci. 292:1115 (2001).
Haller, et al., *Non-Pathogenic Bacteria Elicit a Differential cytokine Response by Intestinal Epithelial Cell/Leucocyte Co-Cultures*, GUT 47:79 (2000).
Walker, W.A., *Role of Nutrients and Bacterial colonization in the Development of Intestinal Host Defense*, J. Pediatr. Gastoenterol. Nutr. 30:S2 (2000).
Isolauri, E., et al., *Probiotics: Effects on Immunity*, Am. J. Clin. Nutr. 73:444S-50S (2001).
Agostoni, et al., *Probiotic Bacteria in Dietetic Products for Infants: A Commentary by the ESPGHAN Committee on Nutrition*, J. Pediatr. Gastro. Nutr. 38:365-374 (Apr. 2004).
Fuller, R., *Probiotics in Man and Animals*, J. Appl. Bacteriol. 66:365-78 (1989).
MacGregor, G., et al., *Yoghurt biotherapy: contraindicated in immunosuppressed patients?* Postgrad Med J. 78:366-367 (2002).
Kirjavainen, P., et al., *Probiotic Bacteria in the Management of Atopic Disease: Underscoring the Importance of Viability*, J. Ped. Gastro. 36:223-227 (2003).
Lawrence, et al., *Possible New Role for NFkB in the Resolution of Inflammation*, Nature Med. 7:1291 (2001).

(Continued)

*Primary Examiner* — Debbie K Ware

(74) *Attorney, Agent, or Firm* — Patterson Intellectual Property Law, P.C.; James R. Cartiglia; Bethany J. Whelan

(57) ABSTRACT

A children's or infant's nutritional product utilizing or containing one or more inactivated probiotics for preventing or reducing systemic and/or respiratory inflammation in a child or infant.

19 Claims, 6 Drawing Sheets

(56) References Cited

OTHER PUBLICATIONS

Yeung, P.S.M., et al., *Species-Specific Identification of Commercial Probiotic Stains*, J. Dairy Sci., 85:1039-1051 (2002).
*Bacterial DNA Reduces Inflammation in Mice*, NIH News, [Online] www.nih.gov/news/pr/feb2004/niaid-03.htm.
Peng, G-C, et al., *The efficacy and safety of heat-killed Lactobacillus paracasei for treatment of perennial allergic rhinitis induced by house-dust mite*, Pediatric Allergy and Immunology, vol. 16, No. 5, Aug. 1, 2005, p. 433-438.
Simakachorn, N., et al., *clinical Evaluation of the Addition of Lyophilized, Heat-Killed Lactobacillus acidophilus LB to Oral Rehydration Therapy in the Treatment of Acute Diarrhea in Children*, Journal of Ped. Gastro. and Nutr., vol. 30, No. 1, Jan. 1, 2000, p. 68-72.
International Search Report of the International Searching Authority for application No. PCT/US2008/054717, International filing date Feb. 22, 2008. Date of mailing Jun. 24, 2008.
Kankaanpaa, P. et al., "Homogenates derived from probiotic bacteria provide down-regulatory signals for peripheral blood mononuclear cells," Food Chemistry 83 (2003) 269-277. Abstract Only.
Zhang, L., et al., "Alive and Dead Lactobacillus rhamnosus GG Decrease Tumor Necorsis Factor-a-Induced Interleukin-8 Production in Caco-2 Cells," J. Nutr. 135: 1752-1756, 2005.
Kaila, M., et al., "Viable versus inactivated lactobacillus strain GG in acute rotavirus diarrhoea," Archives of Disease in Childhood, 1995; 72: 51-53.

* cited by examiner

METHOD FOR THE UTILIZATION OF AND PRODUCT CONTAINING INACTIVATED PROBIOTIC

CROSS-REFERENCE TO RELATED PATENTS AND PATENT APPLICATIONS

This application is a Non-Provisional Patent Application and claims the priority benefit of U.S. Provisional Patent Application Ser. No. 60/904,122, filed Feb. 28, 2007, which is incorporated by reference herein in its entirety.

BACKGROUND OF THE INVENTION (1) Field of the Invention

The present invention relates generally to a product containing and method utilizing at least one inactivated probiotic.

(2) Description of the Related Art

The inflammatory response is an attempt by the body to restore and maintain homeostasis after invasion by an infectious agent, antigen challenge, or physical, chemical or traumatic damage. Localized inflammation is contained in a specific region and can exhibit varying symptoms, including redness, swelling, heat and pain.

While the inflammatory response is generally considered a healthy response to injury, the immune system can present an undesirable physiological response if it is not appropriately regulated. In this situation, the body's normally protective immune system causes damage to its own tissue by treating healthy tissue as if it is infected or abnormal. Alternatively, if there is an injury, the inflammatory response may be out of proportion with the threat causing the injury. When this occurs, the inflammatory response can cause more damage to the body than the agent itself would have produced.

The inflammatory response has been found in part to consist of an increased expression of both pro-inflammatory and anti-inflammatory cytokines. Cytokines are low molecular weight, biologically active proteins involved in the coordination of immunological and inflammatory responses and communication between specific immune cell populations. A number of cell types produce cytokines during inflammatory reactions, including neutrophils, monocytes, and lymphocytes.

Multiple mechanisms exist by which cytokines generated at inflammatory sites influence the inflammatory response. If a pro-inflammatory response is not successfully countered by anti-inflammatory cytokines, however, uncontrolled systemic inflammation can occur.

In contrast to localized inflammation, systemic inflammation is widespread throughout the body. This type of inflammation may include localized inflammation at specific sites, but may also be associated with general "flu-like" symptoms, including fever, chills, fatigue or loss of energy, headaches, loss of appetite, and muscle stiffness. Systemic inflammation can lead to protein degradation, catabolism and hypermetabolism. As a consequence, the structure and function of essential organs, such as muscle, heart, immune system and liver may be compromised and can contribute to multi-organ failure and mortality. Jeschke, et al., *Insulin Attenuates the Systemic Inflammatory Response to Thermal Trauma*, Mol. Med. 8(8): 443-450 (2002). Although enormous progress has been achieved in understanding the mechanisms of systemic inflammation, the mortality rate due to this disorder remains unacceptably high.

Respiratory tract infections are extremely common, especially among infants. In the first year of life, infants are prone to recurrent respiratory tract infections, often experiencing between three and six infections during that year alone. About 6% of infants less than one year of age are hospitalized for lower respiratory tract infections each year in the United States alone.

Respiratory infections and their symptoms can range from mild to severe, depending on the type of virus and the location of the infection. Upper respiratory infections often manifest themselves as common colds, causing inflammation and swelling of the lining of the nose, throat and sinuses. Influenza, commonly known as the flu, is a highly contagious viral infection of the upper respiratory tract. Symptoms of the flu include fever, chills, headache, muscle aches, dizziness, cough, sore throat, runny nose, nausea and diarrhea. Another upper respiratory infection, croup, causes a very deep cough and varying degrees of breathing difficulty, primarily when inhaling.

Lower respiratory infections are generally considered more serious than upper respiratory infections. Respiratory syncytial virus (RSV) is the most frequent cause of lower respiratory tract infections in infants and children younger than four years of age. Van Woensel, J., et al., *Viral Lower Respiratory Tract Infection in Infants and Young Children*, BMJ 327:3640 (2003). This is such a common virus that virtually all children have been infected with RSV by the age of three. In most infants and children, RSV is a mild respiratory infection that is indistinguishable from a common cold. It usually causes nasal stuffiness, nasal discharge and cough.

Protection against RSV involves both T- and B-cell responses, antibody responses (IgM, IgG, and IgA), as well as other immune system responses that are activated by bacterial and viral infections. A link between RSV infection in infancy and the development of recurrent wheezing, asthma and atopy later in childhood has been suggested. Thus, limiting RSV infections could prevent serious respiratory complications which extend well into childhood.

Bronchitis is a lower respiratory infection that affects the bronchial tubes, causing narrowing and swelling due to viral inflammation. Bronchiolitis is similar to bronchitis, but occurs primarily in infants. It is an inflammation of the smaller caliber tubes of the branching network of bronchi. The infection causes labored breathing, frequent and dramatic coughing and wheezing and may require hospitalization.

The lower respiratory infection that is probably the most serious for infants is pneumonia. Pneumonia is caused by an infection in the alveoli, causing them to become filled with fluid, often of a thick purulent nature, that interferes with proper exchange of carbon dioxide. The severity of the pneumonia will depend on the amount of lung tissue involved.

Most upper and lower respiratory infections are caused by viruses for which no specific prevention or treatment is currently available. Some respiratory infections, including influenza, may be prevented with a vaccination. However, even when vaccinations are developed for specific respiratory infections, they are expensive and not universally available. Similarly, drugs to treat these infections have limited availability and are expensive. Thus, it would be useful to provide a non-medicinal method for the treatment or prevention of respiratory infections in infants.

Frequent respiratory tract infections are often associated with acute otitis media (AOM), also known as middle ear infection. AOM is characterized by an acute, short course of inflammation and fluid in the middle ear. AOM can be accompanied by rhinitis, cough, fever, sore throat, ear ache, hypacusis, restlessness, irritability, loss of appetite, vomiting or diarrhea. Purulent otorrhea through a perforated tympanic membrane is also considered to constitute AOM.

Fifty percent of children have had at least one episode of AOM by one year of age. Eighty percent of children have had at least one episode by their third birthday. Between one and three years, 35% of children will have had recurrent episodes of AOM.

AOM can be caused by viruses or bacteria. The most common bacterial strains that cause AOM are *Streptococcus pneumoniae* (35% of cases), *Haemophilus influenzae* (30% of cases) and *Moraxella catarrhalis* (10% of cases). Because bacterial strains frequently cause the infection, AOM is commonly treated through the administration of antibiotics. In fact, more antibiotic prescriptions are written for AOM than for any other disease in infancy.

Often, whether the cytokine response is pro- or anti-inflammatory depends on the balance of individual microorganisms that colonize the intestinal lumen at any particular time. It is well known that the mucosal surface of the intestinal tract is colonized by an enormously large, complex, and dynamic collection of microorganisms. The composition of the intestinal microflora varies along the digestive tract as well as in different micro-habitats, such as the epithelial mucus layer, the deep mucus layer of the crypts, and the surface of mucosal epithelial cells. The specific colonization depends on external and internal factors, including luminally available molecules, mucus quality, and host-microbial and microbial-microbial interactions. Murch, S. H., *Toll of Allergy Reduced by Probiotics*, Lancet, 357:1057-1059 (2001).

These microorganisms, which make up the gut microflora, are actively involved with the immune response. They interact with the epithelium in conditions of mutual beneficial relationships for both partners (symbiosis) or in conditions of benefit for one partner, without being detrimental to the other (commensalisms). Hooper, et al., *How Host-Microbial Interactions Shape the Nutrient Environment of the Mammalian Intestine*, Annu. Rev. Nutr. 22:283-307 (2002). In fact, considerable evidence is emerging which shows a strong interplay or "cross-talk" between the intestinal microflora and the diverse population of cells in the intestinal mucosa. Bourlioux, et al., *The Intestine and its Microflora are Partners for the Protection of the Host: Report on the Danone Symposium "The Intelligent Intestine," held in Paris*, Jun. 14, 2002, Am. J. Clin. Nutr. 78:675 (2003); Hooper, L. V. & Gordon, J. I., *Commensal Host-Bacterial Relationships in the Gut*, Sci. 292:1115 (2001); Haller, et al., *Non-Pathogenic Bacteria Elicit a Differential Cytokine Response by Intestinal Epithelial Cell/Leucocyte Co-Cultures*, GUT 47:79 (2000); Walker, W. A., Role of *Nutrients and Bacterial Colonization in the Development of Intestinal Host Defense*, J. Pediatr. Gastroenterol. Nutr. 30:S2 (2000). Additionally, the gut microflora has been shown to elicit specific immune responses at both a local and systemic level in adults. Isolauri, E., et al., *Probiotics: Effects on Immunity*, Am. J. Clin. Nutr. 73:444S-50S (2001).

The gut microflora in infants is known to be far less developed than that of an adult. While the microflora of the adult human consists of more than $10^{13}$ microorganisms and nearly 500 species, some being harmful and some being beneficial, the microflora of an infant contains only a fraction of those microorganisms, both in absolute number but also species diversity. Infants are born with a sterile gut, but acquire intestinal flora from the birth canal, their initial environment, and what they ingest. Because the gut microflora population is very unstable in early neonatal life, it is often difficult for the infant's gut to maintain the delicate balance between harmful and beneficial bacteria, thus reducing the ability of the immune system to function normally.

It is especially difficult for formula-fed infants to maintain this balance due to the differences between the bacterial species in the gut of a formula-fed and breast-fed infant. The stool of breast-fed infants contains predominantly *Bifidobacterium*, with *Streptococcus* and *Lactobacillus* as less common contributors. In contrast, the microflora of formula-fed infants is more diverse, containing *Bifidobacterium* and *Bacteroides* as well as the more pathogenic species, *Staphylococcus, Escherichia coli*, and *Clostridia*. The varied species of *Bifidobacterium* in the stools of breast-fed and formula-fed infants differ as well. A variety of factors have been proposed as the cause for the different fecal flora of breast-fed and formula-fed infants, including the lower content and different composition of proteins in human milk, a lower phosphorus content in human milk, the large variety of oligosaccharides in human milk, and numerous humoral and cellular mediators of immunologic function in breast milk. Agostoni, et al., *Probiotic Bacteria in Dietetic Products for Infants: A Commentary by the ESPGHAN Committee on Nutrition*, J. Pediatr. Gastro. Nutr. 38:365-374 (April 2004).

Because the microflora of formula-fed infants is so unstable and the gut microflora largely participate in stimulation of gut immunity, formula-fed infants are more likely to develop inflammatory illnesses. Many of the major illnesses that affect infants, including chronic lung disease, periventricular leukomalacia, neonatal meningitis, neonatal hepatitis, sepsis, and necrotizing enterocolitis are inflammatory in nature. Depending on the particular disease, the accompanying inflammation can occur in a specific organ, such as the lung, brain, liver or intestine, or the inflammation can truly be systemic in nature.

For example, chronic lung disease causes the tissues inside the lungs to become inflamed while neonatal meningitis involves inflammation of the linings of the brain and spinal cord. Periventricular leukomalacia is caused by inflammatory damage to the periventricular area in the developing brain. Necrotizing enterocolitis causes inflammation in the intestine that may result in destruction of part or all of the intestine and neonatal hepatitis involves an inflammation of the liver that occurs in early infancy. Sepsis, also known as systemic inflammatory response syndrome, is a severe illness caused by an overwhelming infection of the bloodstream by toxin-producing bacteria. In this disease, pathogens in the bloodstream elicit an inflammatory response throughout the entire body.

Premature and critically ill infants also represent a serious challenge in terms of developing gut immunity and preventing systemic inflammation. Preterm or critically ill infants are often placed immediately into sterile incubators, where they remain unexposed to the bacterial populations to which a healthy, term infant would normally be exposed. This may delay or impair the natural colonization process. These infants are also often treated with broad-spectrum antibiotics, which kill commensal bacteria that attempt to colonize the infant's intestinal tract. Additionally, these infants are often nourished by means of an infant formula, rather than mother's milk. Each of these factors may cause the infant's gut microflora to develop improperly, thus causing or precipitating life-threatening systemic inflammation.

In recent years, the supplementation of probiotic bacteria into the diet of formula-fed infants has been suggested in order to encourage gut colonization with beneficial microorganisms. Probiotic bacteria are living microorganisms that exert beneficial effects on the health of the host. Fuller, R. *Probiotics in Man and Animals*, J. Appl. Bacteriol. 66: 365-78 (1989).

While viable probiotic bacteria may be effective in normalizing the gut microflora, there have been very few published studies assessing their safety in premature and immunosuppressed infants. These special populations have an immature gut defense barrier that increases the risk for translocation of luminal bacteria, causing a potentially heightened risk for infections. In many cases, viable probiotics are not recommended for immunosuppressed patients, post cardiac surgery patients, patients with pancreatic dysfunction, or patients with blood in the stool. At least one death has been reported due to probiotic supplementation in an immunosuppressed individual. MacGregor G., et al. *Yoghurt biotherapy: contraindicated in immunosuppressed patients?* Postgrad Med J. 78: 366-367 (2002).

Thus, for immunosuppressed patients or premature infants, it would be useful to provide a non-viable supplement that may treat or prevent systemic inflammation. A non-viable alternative to active or viable probiotics may have additional benefits such as a longer shelf-life. Active or viable probiotics are sensitive to heat, moisture, and light, and ideally should be refrigerated to maintain viability. Even with these precautions, the shelf-life of a typical probiotic is relatively short. A non-viable alternative to live probiotics would circumvent the necessity of refrigeration and would provide a product having a longer shelf-life. The product could then be distributed to regions of the world without readily available refrigeration. A non-viable alternative to probiotics would additionally provide less risk of interaction with other food components, such as fermentation and changes in the taste, texture, and freshness of the product. Accordingly, it would be beneficial to provide a method for reducing or preventing systemic inflammation in formula-fed infants comprising the administration of inactivated probiotics.

SUMMARY OF THE INVENTION

Briefly, therefore, the present invention is directed to a novel product comprising at least one inactivated probiotic wherein the probiotic in non-viable but the cellular components of the inactivated probiotic retain the same or similar biological reactive attributes as those of the viable or non-inactivated cells of the probiotic.

In other embodiments, the invention is directed to a method of utilizing one or more inactivated strains of probiotics for the same or similar biological reactive benefits as the viable or live probiotic.

In other embodiments, the invention is directed to a method for treating, preventing or reducing systemic and/or respiratory inflammation in a subject, the method comprising administering to the subject a therapeutically effective amount of at least one inactivated probiotic, wherein the probiotic in its viable form is useful for treating, preventing or reducing such systemic and/or respiratory inflammation in a subject.

In other embodiments, the invention is directed to a method for treating, preventing or reducing respiratory inflammation in a subject, the method comprising administering to the subject a therapeutically effective amount of at least one inactivated probiotic, wherein the probiotic in its viable form is useful for such treating, preventing or reducing respiratory inflammation in a subject.

In other embodiments, the invention is directed to a method for reducing or preventing the systemic release of one or more pro-inflammatory cytokines or chemokines in a subject, the method comprising administering to the subject a therapeutically effective amount of at least one inactivated probiotic.

In a particular embodiment, the invention is directed to a method for treating, preventing or reducing systemic inflammation in a subject, the method comprising administering to the subject a therapeutically effective amount of at least one inactivated probiotic in combination with at least one long chain polyunsaturated fatty acid (LCPUFA) and/or at least one viable probiotic. In particular embodiments, the LCPUFA may be docosahexaenoic acid (DHA) or arachidonic acid (ARA).

Among the several advantages found to be achieved by the present invention, it can reduce or prevent systemic or respiratory inflammations. The invention may also reduce inflammation in the liver, plasma, lungs, and intestine. Additionally, the invention reduces or prevents the release of various pro-inflammatory cytokines and chemokines, including interleukin-1β (IL-1β), IL-8, CINC-1, and growth-related oncogene (GRO/KC) levels. As the present invention may be used to improve the inflammatory condition, it may also prevent the onset of deleterious infections or illnesses.

BRIEF DESCRIPTION OF THE DRAWINGS

For a more complete understanding of the present invention, reference is now made to the following descriptions taken in conjunction with the accompanying drawings.

DETAILED DESCRIPTION OF THE PREFERRED EMBODIMENTS

Figure 1:
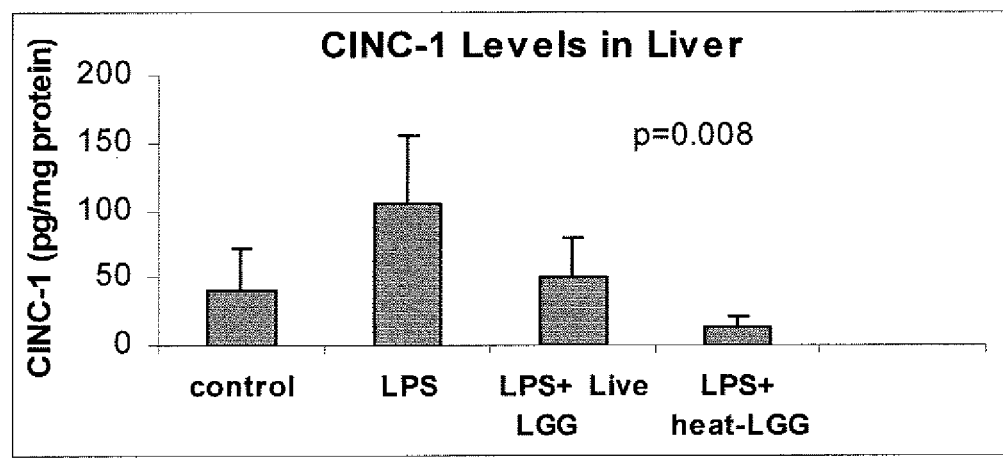
FIG. 1 illustrates the effect of active and inactivated probiotics on cytokine induced neutrophil chemoattractant-1 (CINC-1) peptide production in the liver using enzyme-linked immunosorbent assay (ELISA). Inactivated *Lactobacillus rhamnosus* GG (LGG), an exemplary inactivated probiotic, is labeled as "heat-LGG".

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The following abbreviations are used herein: LGG, *Lactobacillus rhamnosus* GG; LCPUFA, long-chain polyunsaturated fatty acid; LPS, lipopolysaccharide; IL, interleukin; CINC-1, cytokine induced neutrophil chemoattractant-1; GRO/KC, growth-related oncogene, ELISA, enzyme-linked immunosorbent assay; RT-PCR, reverse transcription-polymerase chain reaction, ANOVA, analysis of variance; SD, standard deviation; RMS, rat milk substitute; TLRs, Toll-like receptors; Nuclear Factor kappa B, NF-κB; EPA, eicosapentaenoic acid; DHA, docosahexaenoic acid; ARA, arachidonic acid.

TLRs are a family of vertebrate recognition receptors. They have evolved as key molecules in innate and adaptive immunity. They play a crucial role in the recognition of conserved microbial components. An organism's cell wall components, DNA, and double-stranded RNA are apparently recognized by different TLRs. These bacterial-derived components (whether it be LPC, peptidoglycan or CpG DNA) are natural TLR ligands which retain strong immunomodulatory properties in the absence of the pathogenic consequences which would typically result from normal bacterial proliferation (diarrhea, tissue destruction, systemic inflammation, barrier permeability). The bacterial components typically act on the adaptive immune response whereas the bacteria themselves are sensed by the innate immune response.

The term "probiotic" means a live, active or viable microorganism that exerts beneficial effects on the health of the host.

The term "prebiotic" means a non-digestible food ingredient that stimulates the growth and/or activity of probiotics.

As used herein, the term "treating" means ameliorating, improving or remedying a disease, disorder, or symptom of a disease or condition.

The term "reducing" means to diminish in extent, amount, or degree.

The term "preventing" means to stop or hinder a disease, disorder, or symptom of a disease or condition through some action.

The term "systemic", as used herein, means relating to or affecting the entire body.

The terms "respiratory infection" or "respiratory illness" mean a disease or infection affecting the group of organs responsible for carrying oxygen from the air to the bloodstream and for expelling carbon dioxide.

The terms "inactivated probiotic" or "inactivated LGG" mean that the internal metabolic activity or reproductive ability of the probiotic or LGG organism has been reduced or destroyed. The "inactivated probiotic" or "inactivated LGG", it is believed still retain, at the cellular level, at least a portion their natural TLR ligands which in turn retain at least a portion of their immunomodulatory properties. As used herein, the term "inactivated" is synonymous with "non-viable".

The terms "therapeutically effective amount" refer to an amount that results in an improvement or remediation of the disease, disorder, or symptoms of the disease or condition.

The term "preterm" means an infant born before the end of the 37th week of gestation.

The term "infant" means a postnatal human that is less than about 1 year old.

The term "child" means a human between the ages of about 1 and 12 years old. In certain embodiments, a child is between the ages of about 1 and 6 years old. In other embodiments, a child is between the ages of about 7 and 12 years old.

As used herein, the term "infant formula" means a composition that satisfies the nutrient requirements of an infant by being a substitute for human milk.

In accordance with the present invention, a novel product and method for using a probiotic have been discovered. The product and method comprise the utilization of a therapeutically effective amount of at least one inactivated probiotic and administration thereof to a subject. In some embodiments, the subject is an infant.

Previous attempts to effectively administer inactivated probiotics have met substantial obstacles. For example, Kirjavainen, P., et al., reported that in a comparison of viable and heat-inactivated LGG, nearly 40% of the children supplemented with inactivated LGG experienced severe diarrhea. *Probiotic Bacteria in the Management of Atopic Disease: Underscoring the Importance of Viability*, J. Ped. Gastro. 36: 223-227 (2003). No adverse reactions were reported in the placebo or the viable LGG group. Id. at 225. Because diarrhea is largely associated with inflammation, the Kirjavainen study indicates that inactivated LGG may actually cause gastrointestinal inflammation. In fact, the study notes, "the heat-inactivation process may cause denaturation of surface peptides and expression of heat-shock protein, thus modifying the immunostimulatory properties of LGG in such a way that the heat-inactivated form would induce inflammatory responses and consequently increase gut permeability." Id. at 226. In contrast, the present inventors have developed a novel method for treating or preventing inflammations through the administration of at least one inactivated probiotic by means of ingesting a product containing such inactivated probiotic(s).

The present inventors have discovered that an inactivated probiotic may be utilized to achieve the same or similar beneficial affects on a human ingesting them as that human would obtain by ingesting the same live or viable probiotic. Other than the reproductive and other active properties strictly associated with a living organism, the inactivated probiotics of the present invention retain the cellular and molecular properties and induce the same or similar biological reactive responses in the body of the host ingesting them. As such, the inactivated probiotic of the invention may be any probiotic or combination of any probiotic known in the art.

In other embodiments, the inactivated probiotic may be a member of the genus *Lactobacillus*. For example, the inactivated probiotic may be *L. acidiphilus, L. amylovorus, L. bulgaricus, L. crispatus, L. delbrueckii, L. rhamnosus, L. casei, L. gallinarum, L. fermentum, L. gasseri, L. helveticus, L. jugurti, L. johnsonii, L. leichmannii, L. plantarum, L. reuteri*, or *L. salivarius*. In certain embodiments, the inactivated probiotic may be *L. acidophilus* LA-5®, *L. acidophilus* NCFM, *L. acidophius* AS-1, *L. acidophius* DDS-1, *L. acidophilus* HP10, *L. acidophius* HP100, *L. acidophilus* HP101, *L. acidophius* HP102, *L. acidophilus* HP103, *L. acidophilus* HP104, *L. acidophius* HP15, *L. acidophilus* PIM703, *L. acidophilus* SBT2062, *L. casei* DN-114 001, *L. casei* LC10, *L. casei* PIM61, *L. casei* 431® (CRL431), *L. casei* F19, *L. casei* Shirota, *L. casei* immunitass, *L. crispatus* BG2FO4, *L. delbrueckii* ssp. *bulgaricus*, *L. delbrueckii* ssp. *bulgaricus* 2038, *L. delbrueckii* ssp. *bulgaricus* MR120, *L. delbrueckii* ssp. *bulgaricus* PIM695, *L. plantarum* 299V, *L. reuteri* 1063-S, *L. reuteri* 11284, *L. reuteri* SD2112, *L. reuteri* T-1, *L. reuteri* ATTC 55730, *L. reuteri* SD2112, *L. reuteri* RC-14®, *L. rhamnosus* GG (LGG) ATCC 53013, *L. rhamnosus* GR-1®, *L. rhamnosus* LB21, *L. rhamnosus* R-011, *L. rhamnosus* R-049, *L. rhamnosus* MX1, *L. gasseri* ADH, *L. helveticus*

MR220, *L. helveticus* NCK388, *L. johnsonii* 11088 (NCK 088), *L. johnsonii* La-1, *L. salvarius* UCC500, *L. salvarius* UCC118, or *L. lactis* San.

As set forth above, in a particular embodiment of the invention, the inactivated probiotic may be LGG. LGG is a probiotic strain isolated from healthy human intestinal flora. It was disclosed in U.S. Pat. No. 5,032,399 to Gorbach, et al., which is herein incorporated in its entirety, by reference thereto. LGG is resistant to most antibiotics, stable in the presence of acid and bile, and attaches avidly to mucosal cells of the human intestinal tract. It survives for 1-3 days in most individuals and up to 7 days in 30% of subjects. In addition to its colonization ability, LGG also beneficially affects mucosal immune responses. LGG is deposited with the depository authority American Type Culture Collection under accession number ATCC 53103.

In still other embodiments, the inactivated probiotic may be a member of the genus *Bifidobacterium*. For example, the inactivated probiotic may be *B. animalis*, *B. breve*, *B. infantis*, *B. lactis*, *B. suis*, or *B. longum*. In certain embodiments, the inactivated probiotic may be *Bifidobacterium animalis* ssp. *animalis*, *B. animalis* DN-173 010, *B. animalis* ssp. *lactis* (BB-12®), *B. breve* Yakult, *B. breve* R-070, *B. infantis* BB1, *B. infantis* 35624, *B. lactis* HN019 (DR10), *B. longum* BB46, *B. longum* BBL, or *B. longum* BB536.

As noted, the inactivated probiotic may be *B. animalis* ssp. *lactis* (BB-12®)), available from Chr. Hansen Biosystems, located in Milwaukee, Wis. BB-12® is a Gram-positive anaerobic rod-shaped bacterium, which can be found in the large intestines of most mammals, including humans.

In still other embodiments, the inactivated probiotic may be *Escherichia coli*, *Enterococcus faecium*, *Saccharomyces cerevisiae*, *Lactococcus lactis*, *Bacillus coagulans*, *Pediococcus pentosaceus*, *Pediococcus acidilactici*, *Streptococcus sanguis*, or *Streptococcus thermophilus*. In a particular embodiment, the inactivated probiotic may be *E. coli* Nissle 1917. In another embodiment, the inactivated probiotic may be *Saccharomyces cerevisiae* (boulardii) lyo. In yet another embodiment, the inactivated probiotic may be *Lactococcus lactis* L1A. In a further embodiment, the inactivated probiotic may be *S. thermophilus* TH-4™.

In an embodiment of the invention, more than one inactivated probiotic may be used. Any combination of inactivated probiotics is contemplated in this embodiment provided the combination achieves the intended result. In a particular embodiment, a combination may comprise one or more members of the genus *Bifidobacterium* and one or more members of the genus *Lactobacillus*, such as BB-12® and LGG may be utilized. In a separate embodiment, a combination of BB-12® and LA-5® may be utilized.

In the method of the invention, a therapeutically effective amount of inactivated probiotic is an amount sufficient to reduce or prevent systemic inflammation in a subject. This amount may correspond to between about $1\times10^4$ and $1\times10^{12}$ cell equivalents per kg body weight per day. In another embodiment, the present invention comprises the administration of between about $1\times10^6$ and $1\times10^9$ cell equivalents per kg body weight per day. In yet another embodiment, the present invention comprises the administration of about $1\times10^9$ cell equivalents per kg body weight per day. In still another embodiment, the present invention comprises the administration of about $1\times10^{10}$ cell equivalents per kg body weight per day.

In the present invention, at least one probiotic that has been inactivated is utilized. Inactivation may occur through any method currently known in the art or yet to be developed. The inactivation may be accomplished, for example, via heat treatment, lyophilization, ultraviolet light, gamma radiation, pressure, chemical disruption, or mechanical disruption. For example, the probiotic may be inactivated with heat treatment via storage between 80° C. and 100° C. for 10 minutes. The probiotic may also be inactivated with ultraviolet light via irradiation for 5 minutes at a distance of 5 cm from a 30 Watt UVC lamp. Alternatively, the probiotic may be inactivated with gamma radiation via irradiation with 2 kg-Gray (kGy) using a Cobalt-60 source at a distance of 20 cm.

The form of administration of the inactivated probiotic in the method of the invention is not critical, as long as a therapeutically effective amount is administered. In some embodiments, the at least one inactivated probiotic is administered to a subject via tablets, pills, encapsulations, caplets, gelcaps, capsules, oil drops, or sachets. In another embodiment, the inactivated probiotic is encapsulated in a sugar, fat, or polysaccharide. In yet another embodiment, inactivated probiotic is added to a food or drink product and consumed. The food or drink product may be a children's nutritional product such as a follow-on formula, growing up milk, beverage, milk, yogurt, fruit juice, fruit-based drink, chewable tablet, cookie, cracker, or a milk powder. In other embodiments, the product may be an infant's nutritional product, such as an infant formula or a human milk fortifier.

If the at least one inactivated probiotic is administered via an infant formula, the infant formula may be nutritionally complete and contain suitable types and amounts of lipid, carbohydrate, protein, vitamins and minerals. The amount of lipid or fat typically may vary from about 3 to about 7 g/100 kcal. Lipid sources may be any known or used in the art, e.g., vegetable oils such as palm oil, soybean oil, palmolein, coconut oil, medium chain triglyceride oil, high oleic sunflower oil, high oleic safflower oil, and the like. The amount of protein typically may vary from about 1 to about 5 g/100 kcal. Protein sources may be any known or used in the art, e.g., nonfat milk, whey protein, casein, soy protein, hydrolyzed protein, amino acids, and the like. The amount of carbohydrate typically may vary from about 8 to about 12 g/100 kcal. Carbohydrate sources may be any known or used in the art, e.g., lactose, glucose, corn syrup solids, maltodextrins, sucrose, starch, rice syrup solids, and the like.

Conveniently, commercially available infant formula may be used. For example, Enfamil®, Enfamil® Premature Formula, Enfamil® with Iron, Lactofree®, Nutramigen®, Pregestimil®, and ProSobee® (available from Mead Johnson & Company, Evansville, Ind., U.S.A.) may be supplemented with suitable levels of inactivated probiotics and used in practice of the method of the invention.

In one embodiment of the invention, the at least one inactivated probiotic may be combined with one or more viable probiotics to treat or prevent systemic inflammation in formula-fed infants. Any viable probiotic known in the art may be acceptable in this embodiment provided it achieves the intended result. In a particular embodiment, the viable probiotic may be selected from any of the genera or species of probiotics discussed herein.

If a viable probiotic is administered in combination with the inactivated probiotic, the amount of viable probiotic may correspond to between about $1\times10^4$ and $1\times10^{12}$ colony forming units (cfu) per kg body weight per day. In another embodiment, the viable probiotics may comprise between about $1\times10^6$ and $1\times10^{12}$ cfu per kg body weight per day. In yet another embodiment, the viable probiotics may comprise about $1\times10^9$ cfu per kg body weight per day. In a still further embodiment, the viable probiotics may comprise about $1\times10^{10}$ cfu per kg body weight per day.

In another embodiment of the invention, the at least one inactivated probiotic may be combined with one or more prebiotics to treat or prevent systemic or respiratory inflammation in formula-fed infants. Any prebiotic known in the art will be acceptable in this embodiment provided it achieves the desired result. Prebiotics useful in the present invention may include lactulose, gluco-oligosaccharide, inulin, polydextrose, galacto-oligosaccharide, fructo-oligosaccharide, isomalto-oligosaccharide, soybean oligosaccharides, lactosucrose, xylo-oligosacchairde, and gentio-oligosaccharides.

In yet another embodiment of the present invention, the infant formula may contain other active agents such as LCPUFAs. Suitable LCPUFAs include, but are not limited to, $\alpha$-linoleic acid, $\gamma$-linoleic acid, linoleic acid, linolenic acid, eicosapentanoic acid (EPA), ARA and/or DHA. In an embodiment, an inactivated probiotic is administered in combination with DHA. In another embodiment, an inactivated probiotic is administered in combination with ARA. In yet another embodiment, an inactivated probiotic is administered in combination with both DHA and ARA. Commercially available infant formula that contains DHA, ARA, or a combination thereof may be supplemented with at least one inactivated probiotic and used in the present invention. For example, Enfamil® LIPIL®, which contains effective levels of DHA and ARA, is commercially available and may be supplemented with at least one inactivated probiotic and utilized in the present invention.

In one embodiment, both DHA and ARA are used in combination with at least one inactivated probiotic to treat systemic inflammation in infants. In this embodiment, the weight ratio of ARA:DHA is typically from about 1:3 to about 9:1. In one embodiment of the present invention, this ratio is from about 1:2 to about 4:1. In yet another embodiment, the ratio is from about 2:3 to about 2:1. In one particular embodiment the ratio is about 2:1. In another particular embodiment of the invention, the ratio is about 1:1.5. In other embodiments, the ratio is about 1:1.3. In still other embodiments, the ratio is about 1:1.9. In a particular embodiment, the ratio is about 1.5:1. In a further embodiment, the ratio is about 1.47:1.

In certain embodiments of the invention, the level of DHA is between about 0.0% and 1.00% of fatty acids, by weight.

The level of DHA may be about 0.32% by weight. In some embodiments, the level of DHA may be about 0.33% by weight. In another embodiment, the level of DHA may be about 0.64% by weight. In another embodiment, the level of DHA may be about 0.67% by weight. In yet another embodiment, the level of DHA may be about 0.96% by weight. In a further embodiment, the level of DHA may be about 1.00% by weight.

In embodiments of the invention, the level of ARA is between 0.0% and 0.67% of fatty acids, by weight. In another embodiment, the level of ARA may be about 0.67% by weight. In another embodiment, the level of ARA may be about 0.5% by weight. In yet another embodiment, the level of DHA may be between about 0.47% and 0.48% by weight.

If included, the effective amount of DHA in an embodiment of the present invention is typically from about 3 mg per kg of body weight per day to about 150 mg per kg of body weight per day. In one embodiment of the invention, the amount is from about 6 mg per kg of body weight per day to about 100 mg per kg of body weight per day. In another embodiment the amount is from about 10 mg per kg of body weight per day to about 60 mg per kg of body weight per day. In yet another embodiment the amount is from about 15 mg per kg of body weight per day to about 30 mg per kg of body weight per day.

If included, the effective amount of ARA in an embodiment of the present invention is typically from about 5 mg per kg of body weight per day to about 150 mg per kg of body weight per day. In one embodiment of this invention, the amount varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

If an infant formula is utilized, the amount of DHA in the infant formula may vary from about 5 mg/100 kcal to about 80 mg/100 kcal. In one embodiment of the present invention, DHA varies from about 10 mg/100 kcal to about 50 mg/100 kcal; and in another embodiment, from about 15 mg/100 kcal to about 20 mg/100 kcal. In a particular embodiment of the present invention, the amount of DHA is about 17 mg/100 kcal.

If an infant formula is utilized, the amount of ARA in the infant formula may vary from about 10 mg/100 kcal to about 100 mg/100 kcal. In one embodiment of the present invention, the amount of ARA varies from about 15 mg/100 kcal to about 70 mg/100 kcal. In another embodiment, the amount of ARA varies from about 20 mg/100 kcal to about 40 mg/100 kcal. In a particular embodiment of the present invention, the amount of ARA is about 34 mg/100 kcal.

If an infant formula is used, the infant formula may be supplemented with oils containing DHA and ARA using standard techniques known in the art. For example, DHA and ARA may be added to the formula by replacing an equivalent amount of an oil, such as high oleic sunflower oil, normally present in the formula. As another example, the oils containing DHA and ARA may be added to the formula by replacing an equivalent amount of the rest of the overall fat blend normally present in the formula without DHA and ARA.

If utilized, the source of DHA and ARA may be any source known in the art such as marine oil, fish oil, single cell oil, egg yolk lipid, brain lipid, and the like. In some embodiments, the DHA and ARA are sourced from the single cell Martek oil, DHASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment of the present invention, sources of DHA and ARA are single cell oils as taught in U.S. Pat. Nos. 5,374,567; 5,550,156; and 5,397,591, the disclosures of which are incorporated herein in their entirety by reference. However, the present invention is not limited to only such oils.

In one embodiment, a LCPUFA source which contains EPA is used in combination with at least one inactivated probiotic. In another embodiment, a LCPUFA source which is substantially free of EPA is used in combination with at least one inactivated probiotic. For example, in one embodiment of the present invention, an infant formula containing less than about 16 mg EPA/100 kcal is supplemented with at least one inactivated probiotic and used in the method of the present invention. In another embodiment, an infant formula containing less than about 10 mg EPA/100 kcal is supplemented with at least one inactivated probiotic and used in the method of the present invention. In yet another embodiment, an infant formula containing less than about 5 mg EPA/100 kcal is supplemented with at least one inactivated probiotic and used in the method of the present invention. Another embodiment of the invention includes an infant formula supplemented with at least one inactivated probiotic that is free of even trace amounts of EPA.

It is believed that the provision of a combination of at least one inactivated probiotic with DHA and/or ARA provides complimentary or synergistic effects with regards to the anti-inflammatory properties of formulations containing these agents. While not wishing to be tied to this or any other theory, it is believed that inactivated probiotics impart anti-inflammatory effects, in part, by preventing the ubiquitination of inhibitory-kB (IkB). In a normal cell, IkB binds nuclear factor-kB (NFkB) within the cytoplasm. When ubiquitination of IkB occurs, NFkB is released, enters the nucleus of the cell, and activates genes that are responsible for the inflammatory response. It is this specific interaction and resulting alteration in gene expression that is thought to be involved in the modulation of inflammation. It is believed that inactivated probiotics prevent the ubiquitination of IkB, thereby preventing the release of NFkB and reducing or preventing inflammation.

In contrast, ω-3 fatty acids such as DHA are thought to impart anti-inflammatory action through altering the production of pro-inflammatory, fatty acid-derived, mediators broadly known as eicosanoids. ω-6 fatty acids, such as ARA, which are located in the phospholipid pool of cell membranes, are released during the inflammatory response and liberate a pool of free ARA. This pool of ARA is then acted upon by two classes of enzymes, known as lipoxygenases and cyclooxygenases, which produce a specific spectrum of eicosanoids including the 2-series prostanoids, such as prostaglandins, thromboxanes, and leukotrienes.

These eicosanoids are known to have a plethora of pro-inflammatory actions in many cell types and organs. It is known that diets rich in ω-3 fatty acids, such as EPA and DHA, are competitors for ω-6 fatty acids in several steps of this process and, therefore, moderate the pro-inflammatory effects of ARA. For example, ω-3 fatty acids modulate the elongation of the ω-6 fatty acids into ARA, the incorporation of ARA into the cell membrane phospholipid pool, and the production of pro-inflammatory eicosanoids from ARA. The combination of DHA and ARA, therefore, provides distinct, but complimentary, actions to moderate the inflammatory response in multiple tissues.

In addition, in some embodiments of the invention, viable and inactivated probiotics are administered in combination with one another. The combination of viable and inactivated probiotics is believed to provide complimentary or synergistic effects with regards to the anti-inflammatory properties of formulations containing these agents. While not wishing to be tied to this or any other theory, viable probiotics are thought to impart anti-inflammatory effects in part through interaction with specific receptors, known as Toll-like receptors (TLRs) on the surface of specific immune cells. Direct or indirect interaction between viable probiotics and these receptors initiates an intracellular signal transduction cascade that results in the alteration of gene expression in these target cells. It is this specific interaction and resulting alteration in gene expression and other cellular effects that is thought to be involved in the modulation of inflammation. Thus, because viable and inactivated probiotics are believed to operate through different mechanisms, it is believed that the combination of these components provides complimentary or synergistic anti-inflammatory effects.

In addition, in some embodiments of the invention, at least one viable probiotic, at least one inactivated probiotic, and at least one LCPUFA are administered in combination. Because viable probiotics, inactivated probiotics, and LCPUFAs are each believed to operate through different mechanisms, it is believed that the combination of these components provides complimentary or synergistic effects with regards to the anti-inflammatory properties of formulations containing these agents.

In some embodiments of the present invention, the subject is in need of the treatment, reduction, or prevention of systemic inflammation. The subject may be at risk for systemic inflammation due to genetic predisposition, diet, lifestyle, diseases, disorders, and the like. For example, a preterm or immunosuppressed infant may be at risk for systemic inflammation and may, therefore, be in need of such treatment, reduction, or prevention.

In certain embodiments, the inactivated probiotic may be administered to an infant or child to prevent, treat, or reduce systemic inflammation. In an embodiment, the infant may be less than one year of age. In another embodiment, the child may be between the ages of one and six years old. In yet another embodiment, the child may be between the ages of seven and twelve years old.

In an embodiment of the present invention, the subject is a formula-fed infant. In one embodiment, the infant is formula-fed from birth. In another embodiment, the infant is breast-fed from birth until an age which is less than one year, and is formula-fed thereafter, at which time inactivated probiotic supplementation begins.

In a particular embodiment of the present invention, the method comprises treating or preventing systemic inflammation in a formula-fed preterm infant. In this method, the inactivated probiotic may be administered to the preterm infant in the form of an infant formula, human milk fortifier, or any other suitable form. Additionally, if desired, the inactivated probiotic may be administered to the preterm infant in combination with DHA, ARA, and/or one or more viable probiotics to create a potentially synergistic anti-inflammatory effect.

In an embodiment of the present invention, the inactivated probiotic reduces or prevents the systemic release of one or more pro-inflammatory cytokines or chemokines. As used herein, "pro-inflammatory" cytokines or chemokines include those known in the art to be involved in the up-regulation of inflammatory reactions. Examples include, but are not limited to, TNF-α, IL-1β, IL-6, IL-8, IL-18, and GRO/KC.

Chemokines are a group of cytokines that enable the migration of leukocytes from the blood to the tissues at the site of inflammation. When produced in excess amounts, chemokines can lead to damage of healthy tissue. Growth-related oncogene (GRO/KC) is a chemokine which recruits immune cells to the site of inflammation. It is the human counterpart to rat cytokine-induced neutrophil chemoattractant (CINC-1), and is functionally related to the interleukin-8 family.

In a further embodiment of the invention, inactivated probiotics have been shown to inhibit the translocation of nuclear factor-kB (NFkB). NFkB is a primary transcription factor found in all cell types which is thought to play an important role in onset of inflammation. In most cells, NF-kB is present as a latent, inactive, inhibitory kB (IkB)-bound complex in the cytoplasm. When a cell receives any of a multitude of extracellular signals, such as from cytokines, bacterial antigens, or free radicals, NF-kB rapidly enters the nucleus and activates genes that are responsible for the inflammatory response. It has been shown that inhibition of NFkB at the onset of inflammation results in a decreased inflammatory response. Lawrence, et al., *Possible New Role for NFkB in the Resolution of Inflammation*, Nature Med. 7: 1291 (2001). Thus, the inhibition of NFkB via inactivated probiotic supplementation in the present invention aids in the reduction or prevention of systemic inflammation.

As will be seen in the examples, inactivated probiotics have been shown to reduce systemic inflammation in formula-fed infants. CINC-1 and various cytokine levels in the formula-fed rat infants were reduced to levels similar to that of mother's milk-fed rat infants when supplemented with inactivated probiotics.

As will be seen in the examples, inactivated probiotics have also been shown to significantly reduce IL-8 production, decrease NF-κB translocation, and increase IkB production in the intestinal epithelium. The inventors have surprisingly discovered that inactivated probiotics additionally prevent the ubiquitination of IkB, while viable probiotics do not.

The following examples describe various embodiments of the present invention. Other embodiments within the scope of the claims herein will be apparent to one skilled in the art from consideration of the specification or practice of the invention as disclosed herein.

It is intended that the specification, together with the examples, be considered to be exemplary only, with the scope and spirit of the invention being indicated by the claims which follow the examples. In the examples, all percentages are given on a weight basis unless otherwise indicated.

Example 1

This example illustrates the effect of inactivated probiotic supplementation on systemic inflammation in formula-fed neonatal rat pups. LGG was used as the probiotic in this example.

Materials & Methods

In two separate experiments, Sprague-Dawley (Taconic, Germantown, N.Y.) infant rats were randomly assigned to four gastrostomy feeding groups with five rats per group: a control group (no LPS or LGG), an LPS group, an LPS plus viable LGG group, and an LPS plus inactivated LGG group. Mother-reared rats of the same age were used as reference controls. Gastrostomy feeding, using the rat infant "pup-in-the-cup" model, began on day 7 of life of the rat pups. The gastrostomy feeding tubes were constructed from 24-cm sections of polyethylene tubing that were inserted into the stomach of the pups. The gastrostomy placement was done under isoflurane anesthesia. Timer-controlled syringe pumps were connected to the feeding tubes and were set to feed the rats for the first 20 minutes of every hour at a weight-dependent flow rate.

During a 2-day acclimation period, the gastrostomy-fed rat pups were fed with rat milk substitute (RMS). After the acclimation period, one of the RMS fed groups was given a supplement of $1 \times 10^8$ cell equivalents per kg body weight per day of inactivated LGG. The LGG was inactivated via lethal heat treatment. A second group was given a supplement of $1 \times 10^8$ cfu/L per kg body weight per day of viable LGG. The third group was fed RMS without LGG supplementation of any type. These feedings continued for 6 days. All of the gastrostomy-fed groups received the same quantity of fat and carbohydrates, and the protein component was similar to the quantity required for normal growth. Mother-reared rats of the same age were used as reference controls.

Lipopolysaccharide (LPS) from *Escherichia coli* 0127:B8 (LPS; Sigma, St. Louis, Mo.) was dissolved in water by vortexing at a concentration of 2 mg/ml. The gastrostomy-fed rats were given between 0.25 and 0.5 mg/kg/day of LPS via the gastrostomy tube starting 2 days after the initiation of artificial feeding. The pups were given LPS supplementation for 6 days. This dose was determined in pilot studies to result in occasional shivering, piloerection, and poor weight gain but was not associated with a significant increase in mortality over a 6-day period.

At the end of the 6-day treatment period, the rat pups were euthanized with an overdose of pentobarbital sodium. The small intestine was removed and separated into three parts: the ileum, jejunum, and duodenum, stored at −80° C. for enzyme assays and ELISA, or fixed in 10% neutral buffered formalin for intestinal morphology. Lung, liver and plasma were stored at −80° C. for enzyme assays and ELISA.

Sigmastat statistical software (SPSS, Chicago, Ill.) was used to analyze body weight, ELISA for CINC-1, and cytokine/chemokine multiplex assay results. All data were reported as means±standard deviation (SD). A one-way analysis of variance between groups (ANOVA) was used to determine whether a significant difference was present among all treatment groups. The Holm-Sidak method was performed for pairwise comparisons when the ANOVA was significant at $p<0.05$.

Results & Discussion

Growth

This example illustrates the effect of probiotic administration on the growth of pups after gastrostomy feeding. The rat pups were weighed daily after the gastrostomy feeding and compared to mother-fed reference animals. Mother-fed animals grew more rapidly than the LPS-treated, gastrostomy-fed pups. Providing viable or inactivated probiotics to gastrostomy-fed, LPS treated pups did not improve weight gain.

CINC-1

Viable and inactivated probiotics reduced CINC-1 levels in the present invention. CINC-1 levels were determined by TiterZyme Enzyme Immunometric Assay kits for rat growth-related oncogene/CINC-1 (Assay Designs, Ann Arbor, Mich.). Tissue samples were isolated from cellular extracts of whole tissues in the liver, intestine, plasma, and lung. Absorbance was determined at 450 nm, and concentration was calculated using the equation derived from a linear standard curve.

Figure 2:
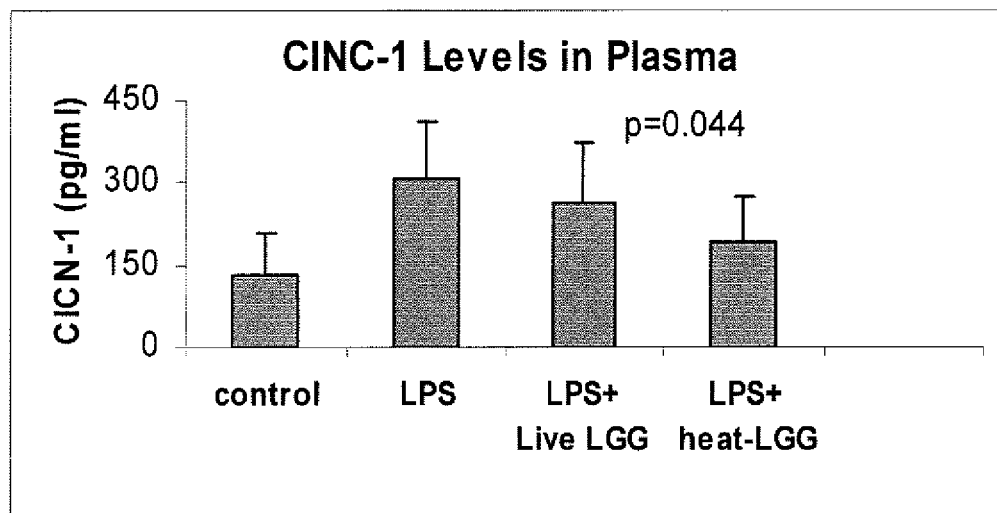
FIG. 2 illustrates the effect of active and inactivated probiotics on CINC-1 peptide production in plasma using ELISA. Inactivated LGG is labeled as "heat-LGG".
Figure 3:
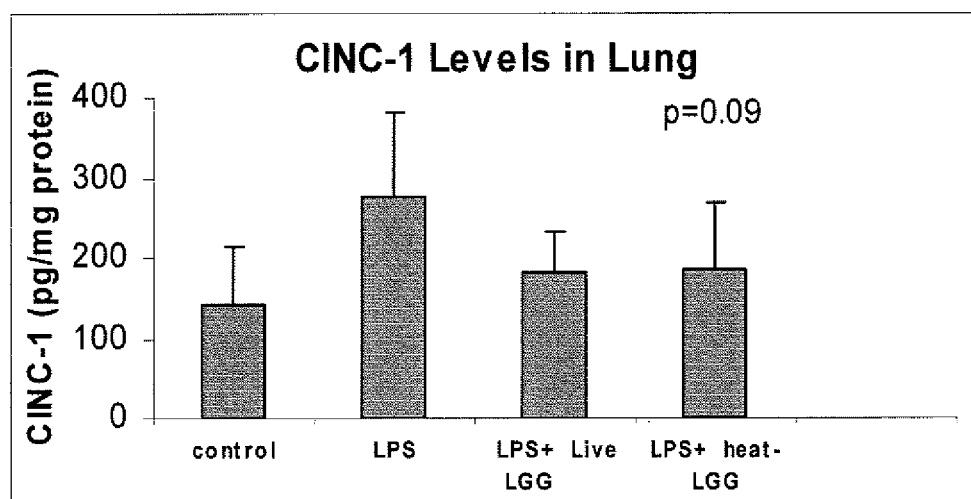
FIG. 3 illustrates the effect of active and inactivated probiotics on CINC-1 peptide production in the lung using ELISA. Inactivated LGG is labeled as "heat-LGG".

As shown in FIGS. 1 through 3, ELISA results showed that LPS increased CINC-1 levels in the liver, lungs, and plasma. Both viable and inactivated probiotics decreased LPS-induced CINC-1 production in the liver (FIG. 1) and plasma (FIG. 2) ($p<0.05$), and also showed a trend ($p=0.09$) in the lung (FIG. 3).

FIG. 1 illustrates that viable probiotic supplementation reduced CINC-1 levels in the liver by approximately 50% when compared to the LPS group. The inactivated probiotic, however, reduced CINC-1 levels in the liver by about 75% when compared to the LPS group. Thus, an inactivated probiotic had a significantly greater reducing effect on liver CINC-1 levels than viable probiotics did, indicating a stronger anti-inflammatory effect. Similarly, FIG. 2 illustrates that CINC-1 levels in the plasma were lower in the inactivated probiotic group than they were in the viable probiotic group. In the lung, both viable and inactivated probiotics reduced CINC-1 levels to a similar degree (FIG. 3).

GRO/KC

Figure 4:
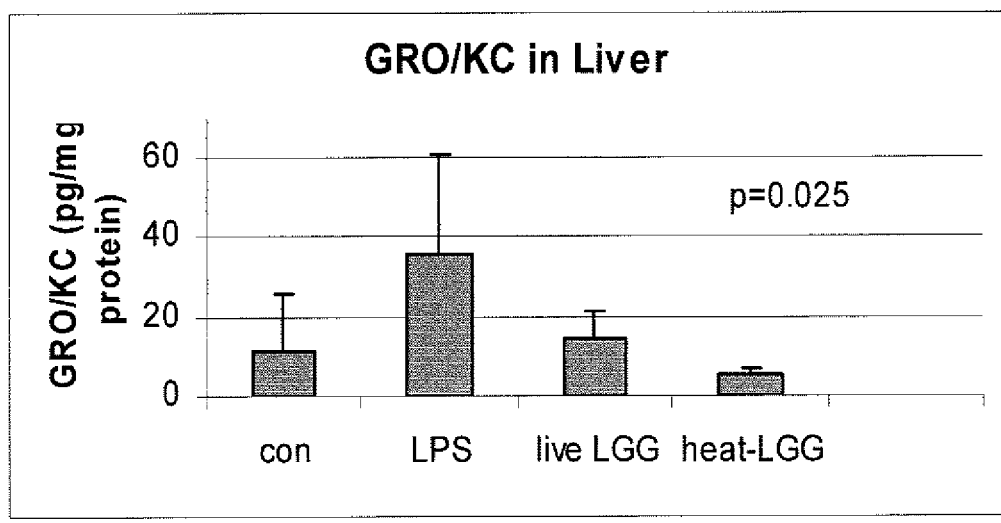
FIG. 4 illustrates the effect of active and inactivated probiotics on growth-related oncogene (GRO/KC) production in the liver using a cytokine multiplex assay. Inactivated LGG is labeled as "heat-LGG".
Figure 5:
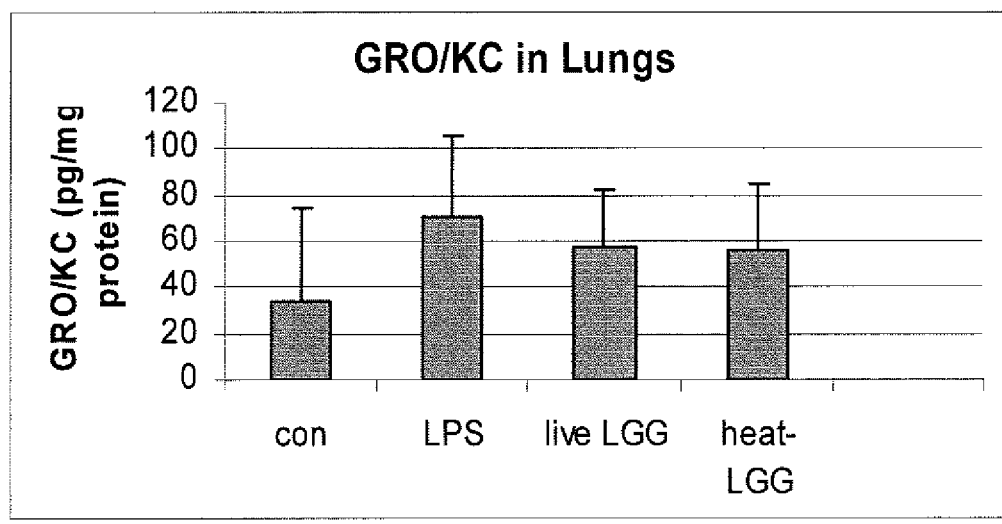
FIG. 5 illustrates the effect of active and inactivated probiotics on GRO/KC production in the lung using a cytokine multiplex assay. Inactivated LGG is labeled as "heat-LGG".

As shown in FIGS. 4 and 5, the cytokine multiplex assay showed similar reductions in GRO/KC levels in the liver and lungs. The inactivated probiotic decreased GRO/KC levels to a greater extent than viable probiotics in the liver, indicating a stronger anti-inflammatory effect (FIG. 4). Both viable and inactivated probiotics reduced GRO/KC levels to a similar degree in the lungs (FIG. 5).

The reduced CINC-1 and GRO/KC levels that were observed in the lung in the present experiment indicate that the anti-inflammatory effect of inactivated probiotics extends to distal organs. Thus, the anti-inflammatory effect of inactivated probiotics is truly systemic in nature.

In the liver, inactivated probiotic supplementation reduced CINC-1 levels to a level which was actually lower than that of mothers milk-fed rat pups. In the lung and plasma, inactivated probiotics reduced CINC-1 levels to a level which was very similar to that of mother's milk-fed rat pups. These results show that inactivated probiotics have the ability to reduce systemic inflammation in a formula-fed infant to a level which is similar to, and in some cases lower than, that of a breast-fed infant.

Cytokines & Chemokines

Viable and inactivated probiotics also reduced cytokine and chemokine levels. Multiplex bead kits were purchased from LINCO Research, Inc. (St. Charles, Mo., USA). Cytokines/chemokines were analyzed by a kit that included: granulocyte-macrophage colony-stimulating factor (GMCSF), interferon-λ (IFN-λ), interleukin-1α (IL-1α), IL-1β, IL-2, IL-4, IL-5, IL-6, IL-8, IL-10, IL-12p70, IL-18, Monocyte Chemoattractant protein-1 (MCP-1), GRO/KC (rat CINC-1), and TNF-α. The multiplex assay was performed according to the manufacturer's specifications. Standard curves for each cytokine/chemokine were generated by using the reference concentrations supplied by the manufacturers. Raw data (mean fluorescent intensity) were analyzed by MasterPlex Quantitation Software (MiraiBio, Inc., Alameda, Calif., USA) to obtain concentration values.

Figure 6:
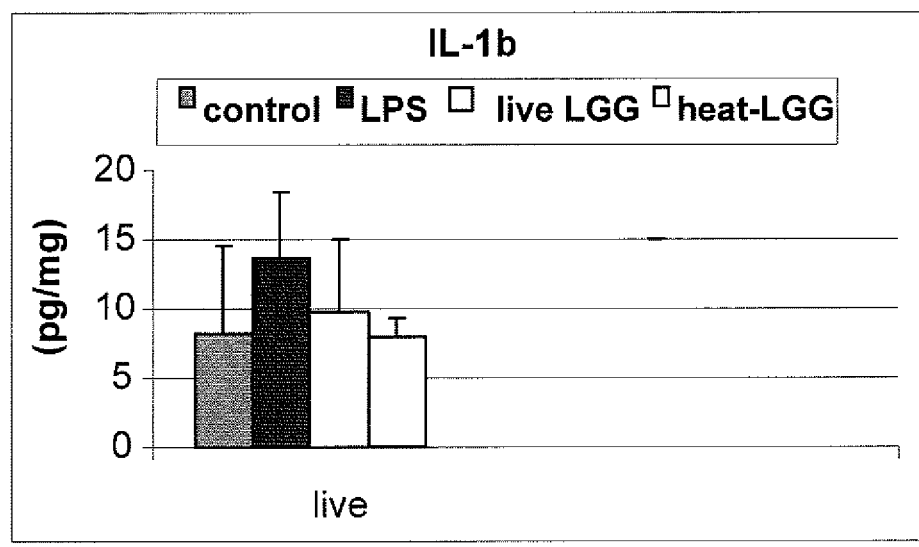
FIG. 6 illustrates the effect of active and inactivated probiotics on interleukin-1β (IL-1β) levels in the liver using a cytokine multiplex assay. Inactivated LGG is labeled as "heat-LGG".

As shown in FIG. 6, IL-1β levels in the liver were significantly higher in gastrostomy-fed, LPS-treated pups than in control pups. Both viable and inactivated probiotics significantly blunted the LPS induced elevation of IL-1β. In fact, inactivated probiotics reduced IL-1β levels to a greater extent than viable probiotic supplementation did. Inactivated probiotics lowered IL-1β expression to a level which was similar to that of the control pups. Thus, this portion of the experiment further illustrates the systemic anti-inflammatory activity of inactivated probiotics.

In conclusion, these results show that inactivated probiotic supplementation reduces systemic inflammation. Further, the results show that inactivated probiotics reduce systemic inflammation in formula-fed infants to a level which is similar to that of breast-fed infants. This is illustrated in the results described herein through comparison of the inactivated probiotic-treated group and the group exclusively fed mother's milk. In several instances, administration of inactivated probiotics results in an inflammatory response that is very similar to that of the mother's milk-fed group.

Example 2

This example further illustrates the effect of inactivated probiotic supplementation on inflammation in formula-fed neonatal rat pups. In this example, LGG was utilized as the probiotic.

Intestinal epithelial cells were pretreated with viable or UV-inactivated LGG at 1×10⁸ cfu/L and then stimulated by Flagellin 500 ng/mL. IL-8 production was measured by ELISA. IkB and ubiquitinated-IkB (UbQ-IkB) expression were measured by Western Blotting and immunoprecipitation. NFkB localization was evaluated by immunofluorescence staining.

During the experiment, Flagellin induced a significant increase in cellular IL-8 production (p<0.05). Cells pretreated with either viable LGG or UV-inactivated LGG and then stimulated by Flagellin showed a significant (p<0.05) change in IL-8, NFkB nuclear translocation, ikB, and UbQ-IkB. The results are shown in Table 1. Arrows pointing upwardly indicate an increase in the parameter, while arrows pointing downwardly indicate a decrease in the parameter.

TABLE 1

Expression Changes Due to Viable or Inactivated Probiotic Supplementation.

| | IL-8 | NFkB Translocation | IkB | UbQ-IkB |
|---|---|---|---|---|
| Flagellin alone | ↑ | ↑ | ↓ | ↑ |
| Viable LGG | ↓ | ↓ | ↑ | ↑ |
| Inactivated LGG | ↓ | ↓ | ↑ | ↓ |

As shown in Table 1, Flagellin induced a significant increase in intestinal epithelial cellular IL-8 production (p<0.05). IL-8 production was significantly downregulated in the presence of both viable and inactivated LGG. In addition, cells stimulated by Flagellin showed NFkB nuclear translocation, which was prevented by both viable and inactivated LGG. Flagellin decreased IkB production, but this effect was reversed by both viable and inactivated LGG pretreatment (p<0.05). Flagellin and viable LGG increased UbQ-IkB (p<0.05), while inactivated LGG decreased UbQ-IkB.

This example illustrates that both viable and inactivated probiotics are effective in decreasing the production of IL-8, a pro-inflammatory cytokine, and thereby have an anti-inflammatory effect. Because Flagellin and the viable probiotic increased UbQ-IkB, but the inactivated probiotic decreased UbQ-IkB, inactivated probiotics likely operate through a mechanism that prevents the ubiquitination of IkB, while viable probiotics likely do not. Thus, this example further illustrates that viable and inactivated probiotics likely operate through different mechanisms and may have synergistic effects when administered together.

The present invention has been shown to reduce inflammation in the liver, plasma, and lungs. As the present invention may be used to improve the inflammatory condition, it may also prevent the onset of deleterious infections or illnesses.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A method for preventing ubiquination of I-kappa-β (Ikβ) in an infant experiencing gastrointestinal inflammation comprising the step of administering a nutritional composition to the infant, wherein the nutritional composition is formulated to deliver from between about $1\times10^4$ to about $1\times10^{10}$ cells of inactivated *Lactobacillus rhamnosus* GG per kg body weight per day.

2. The method of claim 1, wherein the nutritional composition further comprises at least one long-chain polyunsaturated fatty acid (LCPUFA).

3. The method of claim 2, wherein the LCPUFA is selected from the group consisting of docosahexaenoic acid (DHA) and arachidonic acid (ARA).

4. The method of claim 3, wherein the ratio of ARA:DHA is between about 2:3 and about 2:1.

5. The method of claim 3, wherein the docosahexanoic acid is present in the nutritional composition in an amount to provide between about 3 mg to about 150 mg per kg of body weight per day.

6. The method of claim 3, wherein the arachidonic acid is present in the nutritional composition in an amount to provide between about 3 mg to about 150 mg per kg of body weight per day.

7. The method of claim 1, wherein the nutritional composition further comprises a prebiotic.

8. The method of claim 1, wherein the infant is a preterm infant.

9. The method of claim 1, wherein the nutritional composition further comprises a carbohydrate source.

10. The method of claim 1, wherein the nutritional composition further comprises a protein source.

11. The method of claim 1, wherein the nutritional composition further comprises a lipid source.

12. A method reducing the translocation of nuclear factor-kB (NFkB) in an infant experiencing gastrointestinal inflammation, the method comprising the step of administering between about $1\times10^4$ to about $1\times10^{10}$ cells of inactivated *Lactobacillus rhamnosus* GG per kg body weight per day.

13. The method of claim 12, wherein the cells of inactivated *Lactobacillus rhamnosus* GG are formulated in a nutritional composition.

14. The method of claim 12, further comprising the step of administering to the infant between about 3 mg to about 150 mg per kg of body weight per day docosahexanoic acid.

15. The method of claim 12, further comprising the step of administering to the infant between about 3 mg to about 150 mg per kg of body weight per day arachidonic acid.

16. The method of claim 13, wherein the nutritional composition further comprises a prebiotic.

17. The method of claim 12, wherein the infant is a preterm infant.

18. The method of claim 13, wherein the nutritional composition further comprises a carbohydrate source.

19. The method of claim 13, wherein the nutritional composition further comprises a protein source.

* * * * *